(12) United States Patent
Tsuda

(10) Patent No.: US 12,421,121 B2
(45) Date of Patent: Sep. 23, 2025

(54) METHOD FOR PRODUCING HALOGENATED CARBONYL

(71) Applicants: NATIONAL UNIVERSITY CORPORATION KOBE UNIVERSITY, Hyogo (JP); MITSUBISHI GAS CHEMICAL COMPANY, INC., Tokyo (JP)

(72) Inventor: Akihiko Tsuda, Hyogo (JP)

(73) Assignees: NATIONAL UNIVERSITY CORPORATION KOBE UNIVERSITY, Hyogo (JP); MITSUBISHI GAS CHEMICAL COMPANY, INC., Tokyo (JP)

( * ) Notice: Subject to any disclaimer, the term of this patent is extended or adjusted under 35 U.S.C. 154(b) by 824 days.

(21) Appl. No.: 17/639,751

(22) PCT Filed: Sep. 2, 2020

(86) PCT No.: PCT/JP2020/033284
§ 371 (c)(1),
(2) Date: Mar. 2, 2022

(87) PCT Pub. No.: WO2021/045115
PCT Pub. Date: Mar. 11, 2021

(65) Prior Publication Data
US 2022/0289579 A1    Sep. 15, 2022

(30) Foreign Application Priority Data
Sep. 5, 2019    (JP) .................... 2019-162196

(51) Int. Cl.
*C01B 32/80*    (2017.01)

(52) U.S. Cl.
CPC ................... *C01B 32/80* (2017.08)

(58) Field of Classification Search
CPC ...... C01B 32/80; C07C 2601/14; C07C 68/00; C07C 69/09; C07C 273/1809; C07C 69/96; C07C 275/26
See application file for complete search history.

(56) References Cited

U.S. PATENT DOCUMENTS 4,346,210 A    8/1982  Alewelt et al.
4,405,423 A    9/1983  Freund
(Continued)

FOREIGN PATENT DOCUMENTS

JP    6-179743    6/1994
JP    7-10811     1/1995
(Continued)

OTHER PUBLICATIONS

Alippi A et al: "Ultrasound cavitation in sonochemistry: Decomposition of carbon tetrachloride in aqueous solutions of potassium iodide", Ultrasonics, IPC Science and Technology Press Ltd. Guildford, GB, vol. 30, No. 3, 1992, pp. 148-151. (Year: 1992).*

(Continued)

*Primary Examiner* — Deborah D Carr
(74) *Attorney, Agent, or Firm* — Wenderoth, Lind & Ponack, L.L.P.

(57) ABSTRACT

The objective of the present invention is to provide a method for producing a halogenated carbonyl safely and efficiently. The method for producing a halogenated carbonyl according to the present invention is characterized in comprising the step of applying ultrasound to a composition containing a $C_{1-4}$ halogenated hydrocarbon having one or more halogeno groups selected from the group consisting of chloro, bromo and iodo in the presence of oxygen to decompose the $C_{1-4}$ halogenated hydrocarbon.

8 Claims, 1 Drawing Sheet

(56) References Cited

U.S. PATENT DOCUMENTS

| | | | |
|---|---|---|---|
| 5,728,773 | A | 3/1998 | Jing et al. |
| 5,929,169 | A | 7/1999 | Jing et al. |
| 7,138,479 | B2 | 11/2006 | Dhara et al. |
| 11,130,728 | B2 | 9/2021 | Tsuda |
| 11,167,259 | B2 | 11/2021 | Tsuda |
| 2006/0135662 | A1 | 6/2006 | Mullen |
| 2007/0197826 | A1 | 8/2007 | Braun et al. |
| 2011/0245527 | A1 | 10/2011 | Ooms et al. |
| 2015/0285954 | A1 | 10/2015 | Ishizuka et al. |
| 2016/0032046 | A1 | 2/2016 | Shirota et al. |
| 2020/0079723 | A1 | 3/2020 | Tsuda |
| 2020/0122114 | A1 | 4/2020 | Tsuda |
| 2022/0002234 | A1 | 1/2022 | Tsuda et al. |

FOREIGN PATENT DOCUMENTS

| | | | |
|---|---|---|---|
| JP | 8-89975 | | 4/1996 |
| JP | 10-77339 | | 3/1998 |
| JP | 10-291965 | | 11/1998 |
| JP | 11-152328 | | 6/1999 |
| JP | 2000-319230 | | 11/2000 |
| JP | 2001-129397 | | 5/2001 |
| JP | 2001-512515 | | 8/2001 |
| JP | 2003-220332 | | 8/2003 |
| JP | 2003220332 | A * | 8/2003 |
| JP | 2007-527841 | | 10/2007 |
| JP | 2013-181028 | | 9/2013 |
| JP | 2020-83882 | | 6/2020 |
| JP | 7041925 | | 3/2022 |
| SU | 1020006 | | 5/1983 |
| WO | 2012/073970 | | 6/2012 |
| WO | 2014/171367 | | 10/2014 |
| WO | 2015/156245 | | 10/2015 |
| WO | 2018/211952 | | 11/2018 |
| WO | 2018/211953 | | 11/2018 |
| WO | 2020/050368 | | 3/2020 |
| WO | 2020/100970 | | 5/2020 |
| WO | 2020/100971 | | 5/2020 |

OTHER PUBLICATIONS

Extended European Search Report issued Dec. 8, 2023 in corresponding European Patent Application No. 20859957.1.
Alippi, et al, "Ultrasound cavitation in sonochemistry: decomposition of carbon tetrachloride in aqueous solutions of potassium iodide", Ultrasonics, vol. 30, No. 3, 1992, pp. 148-151.
International Search Report issued Nov. 10, 2020 in International (PCT) Application No. PCT/JP2020/033284.
English translation of Office Action issued Jun. 3, 2024 in corresponding Taiwanese Patent Application No. 109130332.
H. Michael Cheung, et al., "Sonochemical Destruction of Chlorinated Hydrocarbons in Dilute Aqueous Solution", Environmental Science & Technology. vol 25, No. 8, 1991, pp. 1510-1512.
Office Action issued Jan. 9, 2025, in Russian Patent Application No. 2023123329, with English translation.
Office Action issued Apr. 20, 2023 in corresponding Chinese Patent Application No. 202080061004.4, with English language translation.
International Search Report issued Apr. 5, 2022 in International (PCT) Application No. PCT/JP2022/002661, with English- language Translation.
Office action issued Nov. 29, 2022 in Japanese Application No. 2022-542485, with English language translation.
Office action issued Sep. 13, 2022 in Japanese Application No. 2022-542485, with English language translation.
Office Action issued Sep. 26, 2024 in Korean Patent Application No. 10-2021-7016978, with English-language Translation.
Office Action issued Jul. 7, 2021 in European Patent Application No. 18 801 749.5.
Extended European Search Report issued Nov. 19, 2020 in European Patent Application No. 18801749.5.
International Search Report issued Jul. 10, 2018 in International (PCT) Application No. PCT/JP2018/017349.
International Search Report issued Nov. 10, 2020 in International Application No. PCT/JP2022/033284.
Office Action issued May 25, 2021 in U.S. Appl. No. 16/605,635.
Extended European Search Report issued Dec. 8, 2023 in European Patent Application No. 20859957.1.
Office Action issued Apr. 20, 2023 in Chinese Patent Application No. 202080061004.4, with English-language Translation.
Office Action issued Jun. 3, 2024 in Taiwanese Patent Application No. 109130332, with English language translation.
C.W. Montgomery, et al., "The Photochemical Decomposition of Phosgene", Contribution From the Chemical Laboratory of ohe University of California, J. Am. Chem. Soc., 1934, vol. 56, pp. 1089-1092.
Yuki Kuwahara, et al., "Photochemical Molecular Storage of C12, HC1, and COC12: Synthesis of Organochlorine Compounds, Salts, Ureas, and Polycarbonate with Photodecomposed Chloroform", Organic Letters, 2012, vol. 14, No. 13, pp. 3376-3379.
Schoorl; van der Berg, "RX-ID 6330183," Chemisches Zentralblatt, 1905, vol. 76, No. II, p. 1623.
Alippi, A. et al., "Ultrasound cavitation in sonochemistry: decomposition of carbon tetrachloride in aqueous solutions of potassium iodide", Ultrasonics, vol. 30, No. 3, 1992, pp. 148-151.
Cheung, Michael H. et al., "Sonochemical Destruction of Chlorinated Hydrocarbons in Dilute Aqueous Solution", Environmental Science & Technology. vol. 25, No. 8, 1991, pp. 1510-1512.
Office Action issued Sep. 12, 2024 in Korean Patent Application No. 10-2021-7016988, with English Translation.
Office Action issued Dec. 18, 2023 in U.S. Appl. No. 17/292,194.
Saudi Arabian Office Action issued Dec. 25, 2023 in Saudi Arabian Patent Application No. 521421871, with English translation.
International Search Report issued Jul. 17, 2018 in International (PCT) Application No. PCT/JP2018/017348.
Kuwahara et al., "Photo-recycling reactions of Halomethanes (1): Synthesis of Urea Derivatives from Chloroform and Primary Amines", Abstracts of the meeting of the Chemical Society of Japan, 92nd, 2012, p. 1251, 2 K2-14, with partial English translation.
Kuwahara et al., "Photo-recycling reactions of Halomethanes (2): Synthesis of Carbonate Derivatives from Chloroform and Phenol Derivatives", Abstracts of the meeting of the Chemical Society of Japan, 92nd, 2012, p. 1251, 2 K2-16, with partial English Translation.
Extended European Search Report issued Nov. 12, 2020 in European Patent Application No. 18802405.3.
Singapore Search Report and Written Opinion issued Feb. 11, 2021 in Singaporean Patent Application No. 11201909670Y.
Search Report and Office Action issued Jun. 15, 2021 in Russian Patent Application No. 2019138715, with English Translation.
Office Action issued Feb. 10, 2022 in Russian Application No. 2021116822, with English-language translation.
Office Action issued Feb. 11, 2022 in Russian Application No. 2021116821, with English-language translation.
Office Action issued May 31, 2024 in U.S. Appl. No. 17/292,194.
Office Action issued Jul. 17, 2022 in Singapore Application No. 11202104285Q.
Office Action issued Aug. 4, 2022 in Chinese Application No. 201980074609.4, with English translation.
Taiwanese Office Action dated Nov. 25, 2022 in Taiwanese Patent Application No. 108141360, with English translation.
Office Action dated Sep. 6, 2023 in Singapore Patent Application No. 11202104285Q.
Written Opinion issued Sep. 6, 2022 in Singapore Application No. 11202104284V.
Notice of Reasons for Refusal issued Sep. 26, 2023 in Japanese Patent Application No. 2020-556165 with English language translation.
Office Action issued Oct. 9, 2023 in Singapore Patent Application No. 11202104284V.
Extended European Search Report issued Nov. 30, 2021 in European Patent Application No. 19883691.8.
Extended European Search Report issued Dec. 9, 2021 in European Patent Application No. 19883406.1.

(56) References Cited

OTHER PUBLICATIONS

Communication pursuant to Article 94(3) EPC issued Jul. 21, 2023 in European Patent Application No. 19883406.1.
Office Action issued Jun. 7, 2023 in Saudi Arabian Patent Application No. 521421868, with English language translation.
Office Action issued Dec. 16, 2022 in Taiwanese Application No. 108141365, with English-language translation.
Office Action issued Jan. 9, 2023 in Chinese Patent Application No. 201980074609.4, with English-language translation.
International Search Report issued Jan. 21, 2020 in International (PCT) Application No. PCT/JP2019/044686.
International Search Report issued Jan. 28, 2020 in International (PCT) Application No. PCT/JP2019/044690.
Ohkuma et al., "Detection of aromatic primary amines by a photochemical reaction with pyridine", The Journal of the Japan Society for Analytical Chemistry, 1975, vol. 24, pp. 385-387.
Herbich et al., "Mechanisms of fluorescence quenching by hydrogen bonding in various aza aromatics", J. Photochem. Photobiol. A: Chem., 1994, vol. 80, pp. 157-160.
Tsurugi et al., Journal of the Society of Rubber Science and Technology, Japan, 1970, vol. 43, No. 5, pp. 337-346, with partial English Translation.
Hoggard et al., "Catalysis of the photodecomposition of carbon tetrachloride in ethanol by an Amberlite anion exchange resin", Journal of Catalysis, 2010, vol. 275, pp. 243-249.
Brooke et al., "A Photocatalyzed Synthesis of Dialkyl Carbonates from Phosgene Generated in situ", Current Catalysis, 2015, vol. 4, No. 1, pp. 12-19.
Office Action issued Mar. 7, 2023 in Chinese Patent Application No. 201980074645.0, with English-language translation.
Office Action issued Mar. 20, 2023 in Taiwanese Patent Application No. 108141365, with English-language translation.
Office Action issued May 9, 2023 in Japanese Patent Application No. 2020-556163, with English-language translation.
Kuwahara et al., "Photochemical molecular storage of Cl2, HCl, and COCl2: Synthesis of organochlorine compounds, salts, ureas, and polycarbonate with photodecomposed chloroform", Organic Letters, 2012, vol. 14, NB. 13, pp. 3376-3379, XP055745410.
Kuwahara et al., "Photochemical molecular storage of Cl2, HCl, and COCl2: Synthesis of organochlorine compounds, salts, ureas, and polycarbonate with photodecomposed chloroform", Organic Letters, 2012, vol. 14, NB. 13, pp. 3376-3379, XP055745415.
Office Action issued May 16, 2025 in Korean Patent Application No. 10-2023-7025702, with English-language Translation.
Office Action issued Feb. 14, 2025 in Korean Patent Application No. 10-2022-7007456, with English-language translation.
Office Action issued Jul. 16, 2025 in Chinese Patent Application No. 202280014107.4, with English-language translation.

* cited by examiner

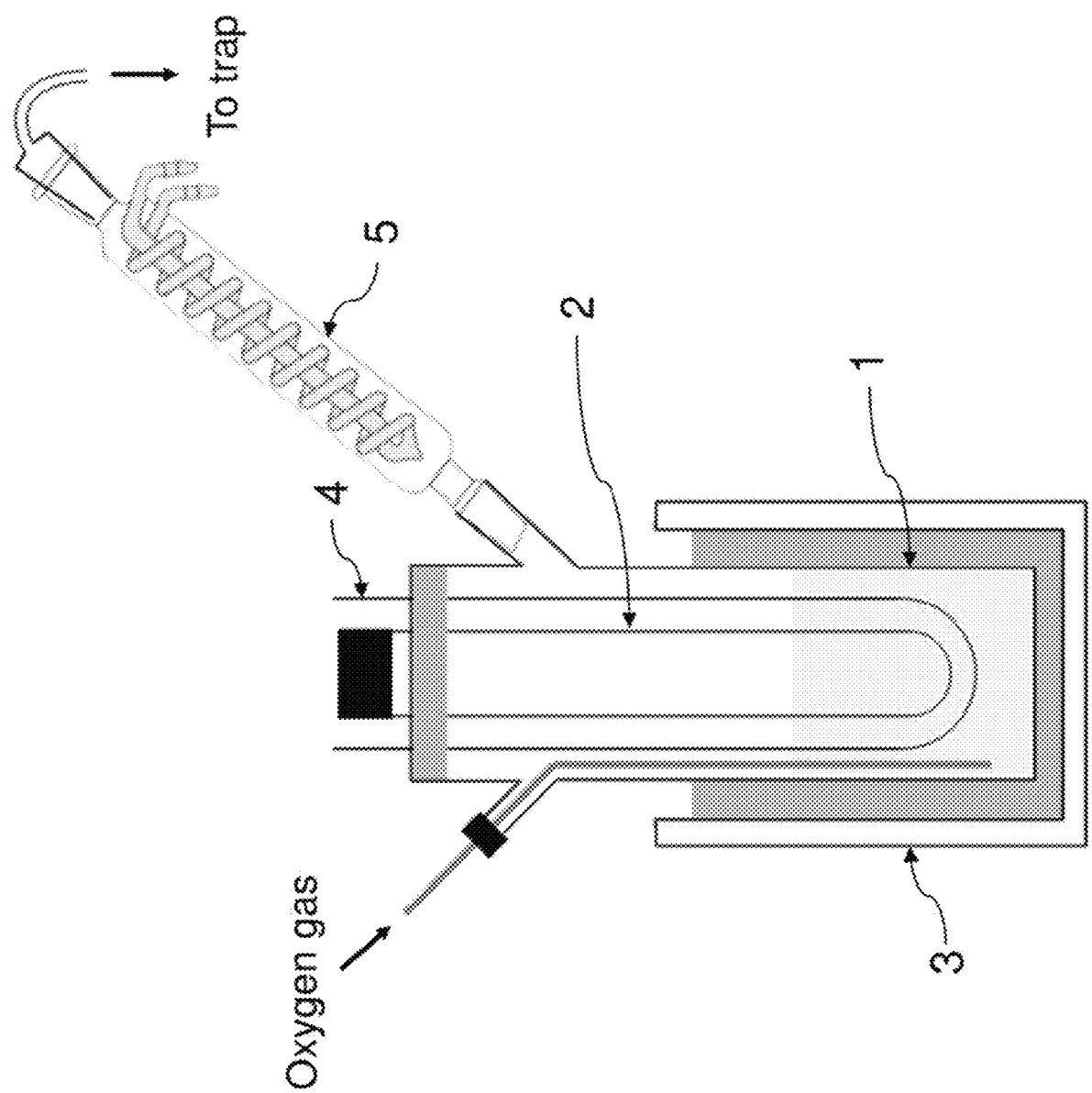

METHOD FOR PRODUCING HALOGENATED CARBONYL

TECHNICAL FIELD

The present invention relates to a method for producing a halogenated carbonyl safely and efficiently.

BACKGROUND ART

A halogenated carbonyl such as phosgene is very important as a synthetic intermediate of various compounds. For example, a carbonate derivative is generally produced from phosgene and a nucleophilic functional group-containing compound.

Phosgene is however very toxic. For example, phosgene easily reacts with water to generate hydrogen chloride and has a history of being used as poisonous gas. Phosgene is generally produced by a high-heat-generating gas-phase reaction between anhydrous chlorine gas and highly pure carbon monoxide in the presence of an activated carbon catalyst. Carbon monoxide used in this reaction is also toxic. The basic process to produce phosgene has not significantly changed since the 1920s. The production of phosgene by such a process requires expensive and huge facilities. In addition, it is essential for plant design to ensure a wide range of safety due to high toxicity of phosgene. Thus, the production cost increases. Furthermore, a large-scale process to produce phosgene may cause many environmental problems. Alternatively, phosgene is produced by decomposing triphosgene with using a base such as triethylamine, but triphosgene is an expensive reagent. It is also known that triphosgene has a potential risk of breakdown into phosgene by some physical stimulus or chemical stimulus and triphosgene itself is highly toxic.

The inventor of the present invention accordingly has developed a method for producing a halogen and/or a halogenated carbonyl by irradiating a light to a halogenated hydrocarbon in the presence of oxygen (Patent document 1). This method is safe, since the produced halogenated carbonyl can be immediately reacted by the coexistence with a reactive substrate compound such as an amine compound and an alcohol compound in this method. In addition, the halogenated carbonyl that is not used for the reaction can be recovered using a trap so as not to be leaked outward. For example, the inventor of the present invention has also developed the method for producing a halogenated carboxylate ester by irradiating a light to the mixture containing a halogenated hydrocarbon and an alcohol in the presence of oxygen (Patent document 2). In addition, the inventor of the present invention has also developed the method for producing a carbonate derivative by irradiating a light to the composition containing a halogenated hydrocarbon, a nucleophilic functional group-containing compound and a base in the presence of oxygen (Patent document 3 and Patent document 4).

PRIOR ART DOCUMENT

Patent Document

Patent document 1: JP 2013-181028 A
Patent document 2: WO 2015/156245
Patent document 3: WO 2018/211952
Patent document 4: WO 2018/211953

DISCLOSURE OF THE INVENTION

Problems to be Solved by the Invention

The inventor of the present invention has developed the method for producing a halogenated carbonyl by irradiating a light to a halogenated hydrocarbon in the presence of oxygen as described above.

A method for producing a halogenated carbonyl such as phosgene more efficiently is required, since a halogenated carbonyl is industrially very important. In particular, a halogenated carbonyl has a problem that a decomposition efficiency of a halogenated hydrocarbon becomes lowered in the case where an alcohol, an amine or water coexists, since an alcohol is used as a stabilizer of chloroform. For example, a chloroform product contains 1% or less of ethanol.

Thus, the objective of the present invention is to provide a method for producing a halogenated carbonyl safely and efficiently.

Means for Solving the Problems

The inventor of the present invention repeated intensive studies in order to solve the above-described problems. As a result, the inventor completed the present invention by finding that a halogenated carbonyl can be efficiently produced by applying ultrasound to a halogenated hydrocarbon in the presence of oxygen.

The present invention is hereinafter described.

[1] A method for producing a halogenated carbonyl, the method comprising the step of applying ultrasound to a composition containing a $C_{1-4}$ halogenated hydrocarbon having one or more halogeno groups selected from the group consisting of chloro, bromo and iodo in the presence of oxygen to decompose the $C_{1-4}$ halogenated hydrocarbon.

[2] The method according to the above [1], wherein a light is further irradiated to the composition.

[3] The method according to the above [1] or [2], wherein a frequency of the ultrasound is 20 kHz or more and 100 kHz or less.

[4] The method according to any one of the above [1] to [3], wherein power of the ultrasound applied to the composition is 0.05 $W/cm^2$ or more and 10 $W/cm^2$ or less per a surface area of the composition.

[5] The method according to above [2], wherein a peak wavelength of the light is included in the range of 180 nm or more and 280 nm or less.

[6] The method according to any one of the above [1] to [5], wherein a $C_{1-2}$ polyhalogenated hydrocarbon is used as the $C_{1-4}$ halogenated hydrocarbon.

[7] The method according to any one of the above [1] to [5], wherein a mixture of dichloromethane and tetrachloromethane is used as the $C_{1-4}$ halogenated hydrocarbon.

Effect of the Invention

A decomposition rate of a halogenated hydrocarbon is increased and a conversion rate to a halogenated carbonyl is improved particularly by an application of ultrasonic in accordance with the method of the present invention. In addition, even if a substance that inhibits the decomposition of a halogenated hydrocarbon, such as an alcohol, is coexistent, the reaction to decompose a halogenated hydrocarbon can proceed. Thus, the present invention is industrially very useful, since a halogenated carbonyl such as phosgene can be produced from a halogenated hydrocarbon safely and efficiently, and a compound produced using a halogenated carbonyl, such as a carbonate derivative, can be eventually produced safely and efficiently.

BRIEF DESCRIPTION OF THE DRAWINGS

FIG. 1 is a schematic diagram to demonstrate one example of the constitution of a reaction apparatus usable in the present invention.

MODE FOR CARRYING OUT THE INVENTION

A halogenated carbonyl is produced by applying ultrasound to a composition containing a $C_{1-4}$ halogenated hydrocarbon having one or more halogeno groups selected from the group consisting of chloro, bromo and iodo in the presence of oxygen to decompose the $C_{1-4}$ halogenated hydrocarbon according to the present invention method.

The $C_{1-4}$ halogenated hydrocarbon usable in the present invention means a hydrocarbon that has a carbon number of 1 or more and 4 or less and that has one or more halogeno groups selected from the group consisting of chloro, bromo and iodo. The $C_{1-4}$ halogenated hydrocarbon may be decomposed by ultrasound and oxygen to be a halogenated carbonyl.

The $C_{1-4}$ halogenated hydrocarbon means an alkane, an alkene or an alkyne that is substituted with one or more halogeno groups selected from the group consisting of chloro, bromo and iodo and that has a carbon number of 1 or more and 4 or less. The $C_{1-4}$ halogenated hydrocarbon may be decomposed by ultrasound and oxygen to play a role as a halogenated carbonyl in the present invention as described above. The $C_{1-4}$ halogenated hydrocarbon is preferably a $C_{1-2}$ halogenated hydrocarbon and more preferably a halogenated methane. When the carbon number is 2 or more and 4 or less, an alkene or an alkyne having one or more unsaturated bonds is preferred in order to be decomposed more easily. A $C_{1-4}$ polyhalogenated hydrocarbon having 2 or more halogeno groups is preferred, and a $C_{1-2}$ polyhalogenated hydrocarbon is more preferred. In addition, a $C_{1-4}$ halogenated hydrocarbon having 2 or more halogeno groups on the same carbon is preferred, though the halogeno group may be possibly transferred.

An example of the $C_{1-4}$ halogenated hydrocarbon specifically includes a halogenated methane such as dichloromethane, chloroform, dibromomethane, bromoform, iodomethane and diiodomethane; a halogenated ethane such as 1,1,2-trichloroethane, 1,1,1-trichloroethane, 1,1,2,2-tetrachloroethane and 1,1,1,2-tetrachloroethane; a halogenated propane such as 1,1,1,3-tetrachloropropane; a perhalogenated alkane such as tetrachloromethane, tetrabromomethane, tetraiodomethane, hexachloroethane and hexabromoethane; and a perhalogenated ethene such as 1,1,2,2-tetrachloroethene and 1,1,2,2-tetrabromoethene.

The $C_{1-4}$ halogenated hydrocarbon may be appropriately selected depending on the target chemical reaction and the target product. One of the $C_{1-4}$ halogenated hydrocarbon may be used by itself, or two or more of the $C_{1-4}$ halogenated hydrocarbons may be used in combination. It is preferred that only one kind of the $C_{1-4}$ halogenated hydrocarbon is used depending on the target compound. The $C_{1-4}$ halogenated hydrocarbon that is liquid under an atmospheric pressure and an atmospheric temperature or under an atmospheric pressure and a reaction temperature can be also used as a solvent. The $C_{1-4}$ halogenated hydrocarbon having chloro is preferred.

An example of a combination of 2 or more kinds of the $C_{1-4}$ halogenated hydrocarbons includes a mixture of dichloromethane and tetrachloromethane. Tetrachloromethane is produced as a by-product during the production of dichloromethane and chloroform, but the use of tetrachloromethane is prohibited in principle in Japan for purposes other than test, research and analysis. On the one hand, tetrachloromethane can be advantageously treated in combination with dichloromethane in the present invention. When dichloromethane and tetrachloromethane are combined, a ratio thereof may be appropriately adjusted. For example, a ratio of a mole number of tetrachloromethane to a total mole number of dichloromethane and tetrachloromethane may be adjusted to 0.1 or more and 0.6 or less.

Chloroform is the most preferred as the $C_{1-4}$ halogenated hydrocarbon used in the present invention method, since chloroform is also a widely used solvent and is inexpensive. For example, the $C_{1-4}$ halogenated hydrocarbon may be recovered to be used again after being once used as a solvent. It is preferred that such a used $C_{1-4}$ halogenated hydrocarbon is purified to some extent for use, since if a large amount of an impurity and water are contained, the reaction may be possibly inhibited. For example, it is preferred that water and a water-soluble impurity are removed by washing with water and then the $C_{1-4}$ halogenated hydrocarbon is dried by anhydrous sodium sulfate, anhydrous magnesium sulfate or the like. An excessive purification by which the productivity becomes less is not needed, since the reaction may proceed even in the case where about 1 vol % of water is contained. The water content is more preferably 0.5 vol % or less, even more preferably 0.2 vol % or less, and even more preferably 0.1 vol % or less. The $C_{1-4}$ halogenated hydrocarbon to be reused may contain a decomposed product of the $C_{1-4}$ halogenated hydrocarbon.

A usage amount of the $C_{1-4}$ halogenated hydrocarbon may be appropriately adjusted as long as a sufficient amount of a halogenated carbonyl can be produced, and for example, 0.1 times or more by mole of the $C_{1-4}$ halogenated hydrocarbon to a reactive substrate compound to be reacted with the produced halogenated carbonyl may be used. The upper limit of the usage amount of the $C_{1-4}$ halogenated hydrocarbon is not particularly restricted, and for example, the usage amount can be adjusted to 200 times or less by mole to the reactive substrate compound. The usage amount is preferably 1 time or more by mole, 5 times or more by mole or 10 times or more by mole, more preferably 20 times or more by mole, and even more preferably 25 times or more by mole. When the $C_{1-4}$ halogenated hydrocarbon can be used as a solvent, 50 times or more by mole of the $C_{1-4}$ halogenated hydrocarbon can be used. The usage amount is preferably 150 times or less by mole or 100 times or less by mole. The specific usage amount of the $C_{1-4}$ halogenated hydrocarbon may be determined by a preliminary experiment or the like.

A solvent may be added to the composition containing the $C_{1-4}$ halogenated hydrocarbon. In particular, when the $C_{1-4}$ halogenated hydrocarbon is not liquid under an atmospheric temperature and an atmospheric pressure, a solvent that can appropriately dissolve the $C_{1-4}$ halogenated hydrocarbon and that does not inhibit the decomposition of the $C_{1-4}$ halogenated hydrocarbon is preferred. An example of the solvent includes a ketone solvent such as acetone, methyl ethyl ketone, methyl isobutyl ketone and cyclohexanone; an aliphatic hydrocarbon solvent such as n-hexane; an aromatic hydrocarbon solvent such as benzene, toluene, xylene and benzonitrile; an ether solvent such as diethyl ether, tetrahydrofuran and dioxane; and a nitrile solvent such as acetonitrile.

An oxygen source may be a gas containing oxygen, and for example, air or purified oxygen may be used. Purified oxygen may be mixed with an inert gas such as nitrogen and argon to be used. Air can be used in terms of cost and easiness. An oxygen content in the gas used as an oxygen source is preferably about 15 vol % or more and about 100 vol % or less in terms of high decomposition efficiency of the $C_{1-4}$ halogenated hydrocarbon by ultrasound application. Also, substantially oxygen only other than an inevitable impurity is preferably used. The oxygen content may be appropriately determined depending on the kind of the $C_{1-4}$ halogenated hydrocarbon or the like. For example, when a $C_{1-4}$ chlorohydrocarbon such as dichloromethane, chloroform and tetrachloroethylene is used as the $C_{1-4}$ halogenated hydrocarbon, the oxygen content is preferably 15 vol % or more and 100 vol % or less. When a $C_{1-4}$ bromohydrocarbon compound such as dibromomethane and bromoform is used, the oxygen content is preferably 90 vol % or more and 100 vol % or less. Even when oxygen having an oxygen content of 100 vol % is used, the oxygen content can be controlled in the above-described range by adjusting a flow rate of oxygen into the reaction system. A manner to supply a gas containing oxygen is not particularly restricted, and the gas may be supplied from an oxygen tank equipped with a flow rate adjustor into the reaction system or from an oxygen generating device into the reaction system.

The phrase "in the presence of oxygen" means any one of the state that the $C_{1-4}$ halogenated hydrocarbon is contacted with oxygen and the state that there is oxygen in the composition. Thus, the reaction of the present invention may be carried out under a stream of a gas containing oxygen or in a two-phase system composed of a gas phase containing oxygen and a liquid phase containing the $C_{1-4}$ halogenated hydrocarbon without continuously supplying oxygen, and it is preferred to supply a gas containing oxygen into the composition by bubbling in order to improve the yield of the product.

An amount of an oxygen-containing gas may be appropriately determined depending on the amount of the $C_{1-4}$ halogenated hydrocarbon, a shape of the reaction vessel or the like. For example, an amount of the gas supplied to the reaction vessel per 1 minute to the $C_{1-4}$ halogenated hydrocarbon in the reaction vessel is preferably 5 times or more by volume. The ratio is more preferably 25 times or more by volume, and even more preferably 50 times or more by volume. The upper limit of the ratio is not particularly restricted, and the ratio is preferably 500 times or less by volume, more preferably 250 times or less by volume, and even more preferably 150 times or less by volume. The amount of oxygen supplied to the reaction vessel per 1 minute to the $C_{1-4}$ halogenated hydrocarbon in the reaction vessel may be adjusted to 5 times or more by volume and 25 times or less by volume. When an amount of the supplied gas is excessively large, the $C_{1-4}$ halogenated hydrocarbon may be possibly volatilized, but when the amount is excessively small, it may possibly become difficult to promote the reaction.

Ultrasound is applied to the composition containing the $C_{1-4}$ halogenated hydrocarbon in the presence of oxygen in the present invention method. A halogenated carbonyl may be produced by reacting oxygen and a radical produced by decomposition of the $C_{1-4}$ halogenated hydrocarbon. Oxygen may be atomized by ultrasound, and the radical reaction may be promoted by the cavitation effect due to ultrasound.

Ultrasound generally means a sound wave having a frequency of 20 kHz or more. Ultrasound having an appropriate frequency in the range may be selected in the present invention, and the frequency of the ultrasound used in the present invention is preferably 20 kHz or more and 1500 kHz or less. When the frequency is 20 kHz or more, the production efficiency of a halogenated carbonyl may be improved more surely. The frequency is preferably 30 kHz or more, and preferably 1000 kHz or less or 500 kHz or less, more preferably 200 kHz or less or 150 kHz or less, even more preferably 100 kHz or less. Ultrasound may be continuously applied or intermittently applied.

A method for applying ultrasound to the composition containing the $C_{1-4}$ halogenated hydrocarbon is not particularly restricted. For example, the reaction vessel containing the composition may be immersed in a water bath of an ultrasound washer or a water bath in which an oscillator of an ultrasound-generating device is immersed, or an oscillator of an ultrasound-generating device may be immersed in the composition. Ultrasound can be applied to the composition directly or nearly directly by the above-described embodiments.

The strength of the ultrasound to be applied may be appropriately adjusted. The strength can be adjusted by the power of the ultrasound-generating device to be used, since ultrasound can be directly or nearly directly applied to the composition as described above. For example, the power of an ultrasound-generating device per the surface area of the composition to which ultrasound is applied is preferably 0.05 W/cm$^2$ or more and 10 W/cm$^2$ or less. When the power is 0.05 W/cm$^2$ or more, the production efficiency of a halogenated carbonyl can be improved more surely. When the power is 10 W/cm$^2$ or less, degassing of oxygen from the composition can be prevented more surely. The power is more preferably 0.1 W/cm$^2$ or more, even more preferably 0.5 W/cm$^2$ or more, and more preferably 5 W/cm$^2$ or less, even more preferably 1 W/cm$^2$ or less or 0.5 W/cm$^2$ or less.

The temperature at which ultrasound is applied to the composition may be appropriately adjusted, and may be adjusted to, for example, −20° C. or higher and 60° C. or lower. When the temperature is −20° C. or higher, the $C_{1-4}$ halogenated hydrocarbon may be decomposed more surely to efficiently produce a halogenated carbonyl. When the temperature is 60° C. or lower, the concentrations of oxygen and the produced halogenated carbonyl in the composition may be maintained more surely. The temperature is preferably −10° C. or higher, more preferably 0° C. or higher or 10° C. or higher, and preferably 50° C. or lower or 40° C. or lower, more preferably 30° C. or lower.

Ultrasound may be applied to the composition until the $C_{1-4}$ halogenated hydrocarbon is decomposed to produce a sufficient amount of a halogenated carbonyl. When the composition contains a reactive substrate compound that reacts with a halogenated carbonyl, ultrasound may be applied to the composition until the reaction sufficiently proceeds. For example, ultrasound may be applied to the composition until all of the reactive substrate compound is substantively consumed. The specific application time may be determined by a preliminary experiment and may be adjusted to, for example, 10 minutes or more and 10 hours or less. The application time is preferably 20 minutes or more, more preferably 30 minutes or more, and preferably 5 hours or less, more preferably 3 hours or less or 2 hours or less.

The decomposition of the $C_{1-4}$ halogenated hydrocarbon can be further promoted to further improve the production efficiency of a halogenated carbonyl by irradiating a light in addition to application of ultrasound to the composition containing the $C_{1-4}$ halogenated hydrocarbon in the present invention method.

The light irradiated to the composition is preferably a light containing a short wavelength light having high energy, more preferably a light containing ultraviolet light, and specifically preferably a light having a peak wavelength included in a range of 180 nm or more and 500 nm or less. The peak wavelength of the high energy light may be appropriately determined depending on the kind of the $C_{1-4}$ halogenated hydrocarbon, and is more preferably 400 nm or less and even more preferably 300 nm or less. When the peak wave length of the applied light is included in the above-described range, the $C_{1-4}$ halogenated hydrocarbon can undergo oxidative photodecomposition in an efficient fashion. For example, a light having a peak wavelength included in UV-B wavelength range of 280 nm or more and 315 nm or less and/or a light having a peak wavelength included in UV-C wavelength range of 180 nm or more and 280 nm or less can be used, and a light having a peak wavelength included in UV-C wavelength range of 180 nm or more and 280 nm or less is preferably used.

A means for means for the light is not particularly restricted as long as the light having the above-described wavelength can be irradiated by the means. An example of a light source containing a light having such a wave length range includes sunlight, low pressure mercury lamp, medium pressure mercury lamp, high pressure mercury lamp, ultrahigh pressure mercury lamp, chemical lamp, black light lamp, metal halide lamp and LED lamp. A low pressure mercury lamp is preferably used in terms of a reaction efficiency and a cost.

The condition such as a strength of the light to be irradiated and an application time may be appropriately determined depending on the kind and the usage amount of the $C_{1-4}$ halogenated hydrocarbon. For example, a light strength at a shortest distance position of the composition from the light source is preferably 1 mW/cm$^2$ or more and 50 mW/cm$^2$ or less. An embodiment to irradiate the light is also not particularly restricted, and any embodiments, for example, the light is continuously irradiated from the initiation to the completion of the reaction, photo-irradiation and no photo-irradiation are alternatingly repeated and the light is irradiated only for a predetermined time from the initiation of the reaction, can be adopted. A shortest distance between the light source and the composition is preferably 1 m or less, more preferably 50 cm or less, and even more preferably 10 cm or less or 5 cm or less. The lower limit of the shortest distance is not particularly restricted and may be 0 cm, in other words, the light source may be immersed in the composition. When a light is applied from the lateral side of the reaction vessel, the shortest distance may be adjusted to 1 cm or more or 2 cm or more.

A halogenated carbonyl may be produced by oxidative decomposition of the $C_{1-4}$ halogenated hydrocarbon in the above-described step. When there is a reactive substrate compound in the reaction system, the reactive substrate compound may react with not only the produced halogenated carbonyl [X—C(=O)—X wherein X is one or more halogeno groups selected from the group consisting of chloro, bromo and iodo.] but also a halogenated carbonyl-like compound, which plays a role similarly to the halogenated carbonyl. Such a halogenated carbonyl-like compound is included in the halogenated carbonyl according to the present invention.

The produced halogenated carbonyl may not be isolated to be reacted with a reactive substrate compound in the reaction system, since a halogenated carbonyl is toxic. For example, when an alcohol compound is added to the composition containing the $C_{1-4}$ halogenated hydrocarbon, the alcohol compound immediately reacts with the halogenated carbonyl produced by the oxidative decomposition of the $C_{1-4}$ halogenated hydrocarbon to produce a halogenated formate ester. When a base is added in addition to an alcohol compound and/or an amine compound, a carbonate compound, a urea compound or a urethane compound is produced. In particular, when a base and a diol compound and/or a diamine compound are added, a polycarbonate compound, a polyurea compound or a polyurethane compound is produced.

A reaction apparatus usable in the present invention method is exemplified by a reaction vessel equipped with an ultrasound-applying means. One embodiment of a reaction apparatus usable in the production method of the present invention is shown in FIG. 1. The reaction apparatus shown in FIG. 1 has a light irradiating means 2 in a reaction vessel 1, and the reaction vessel 1 is immersed in a water bath 3 of an ultrasound-generating device. At least the $C_{1-4}$ halogenated hydrocarbon is added into the reaction vessel 1, and a gas containing at least oxygen is supplied into the reaction vessel 1 or a gas containing oxygen is blown into the reaction mixture to cause bubbling. Ultrasound is applied to the reaction mixture through the water bath 3 from the ultrasound-generating device for the reaction. A light may be further irradiated to the reaction mixture by a light-irradiating means 2. The light-irradiating means 2 is preferably covered with a jacket 4 in order to prevent corrosion due to an acid generated by decomposition of the $C_{1-4}$ halogenated hydrocarbon. The jacket 4 is composed of glass or the like. The temperature of the reaction mixture is preferably controlled to be constant or nearly constant by the water bath 3. The reaction mixture is not needed to be stirred, since the reaction mixture becomes homogenous by applying ultrasound. The reaction vessel 1 is preferably equipped with a cooling tube 5, since the reaction is often thermogenic. Even when the produced halogenated carbonyl is vaporized due to heat, the halogenated carbonyl can be liquefied by the cooling tube 5 to be recirculated to the reaction mixture. The gas emitted from the reaction vessel 1 is preferably introduced into a trap to capture the halogenated carbonyl in order to prevent the leak of the excessive halogenated carbonyl outside the reaction system.

The present application claims the benefit of the priority date of Japanese patent application No. 2019-162196 filed on Sep. 5, 2019. All of the contents of the Japanese patent application No. 2019-162196 filed on Sep. 5, 2019, are incorporated by reference herein.

EXAMPLES

Hereinafter, the examples are described to demonstrate the present invention more specifically, but the present invention is in no way restricted by the examples, and the examples can be appropriately modified to be carried out within a range that adapts to the contents of this specification. Such a modified example is also included in the range of the present invention.

Example 1: Promoting Effect of Phosgene Production by Ultrasound and High Energy Light

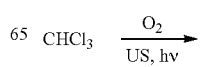

-continued

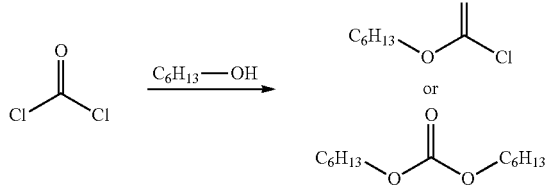

A quartz glass jacket having a diameter of 30 mm was centrally inserted in a cylindrical reaction vessel having a diameter of 42 mm, and a low pressure mercury lamp ("UVL20PH-6" manufactured by SEN Light, 20 W, φ24× 120 mm, wave length: 185 to 600 nm, peak wave length: 254 nm) was further inserted in the quartz glass jacket. Purified chloroform (20 mL, 250 mmol) was added into the reaction vessel. The reaction vessel was immersed in the water bath of an ultrasound washer ("1510J-MT" manufactured by BRANSONIC), and oxygen gas was blown into the chloroform by bubbling at 0.5 L/min with applying ultrasound of 70 W and 42 kHz and irradiating a high energy light from the low pressure mercury lamp at 20° C. for the reaction for 1 hour. Then, 1-hexanol (12.5 mL, 100 mmol) was added in order to estimate an amount of the produced phosgene. The gas discharged from the reaction vessel was introduced into a hexanol trap to capture phosgene in the gas during the reaction.

The reaction mixture after the reaction was analyzed by $^1$H-NMR to estimate the amounts of the produced chloroformate and carbonate. The hexanol solution in the trap was also analyzed by $^1$H-NMR to estimate the amounts of the produced chloroformate and carbonate. The amount of the produced phosgene and the yield of phosgene to the used chloroform were calculated under the presumption that all of the produced phosgene was reacted with 1-hexanol to be converted to a chloroformate or a carbonate.

In addition, an amount of the produced phosgene was similarly estimated in the condition that ultrasound was not applied for comparison. The result is shown in Table 1.

TABLE 1

| Amount of $CHCl_3$ | Ultrasound application | Yield (vs chloroform) |
|---|---|---|
| 20 mL (250 mmol) | OFF | 11% |
| 20 mL (250 mmol) | ON | 27% |

It was demonstrated by the result shown in Table 1 that chloroform is decomposed to produce phosgene by irradiating a high energy light only but an amount of the produced phosgene from chloroform is increased 2 times or more by applying ultrasound in addition to irradiation of a high energy light.

Example 2: Promoting Effect of Phosgene Production by Ultrasound and High Energy Light Purified chloroform (20 mL, 250 mmol) and 1-hexanol (1.25 mL, 10 mmol) were added in the reaction vessel of the reaction system used in Example 1. The reaction vessel was immersed in the water bath of an ultrasound washer ("1510J-MT" manufactured by BRANSONIC), and oxygen gas was blown by bubbling at 0.5 L/min with applying ultrasound of 70 W and 42 kHz and irradiating a high energy light from the low pressure mercury lamp at 20° C. for the reaction for 30 minutes. Then, the photo-irradiation was stopped for 30 minutes. The reaction was similarly carried out except that the cycle was repeated 2 times. Next, the temperature was increased to 50° C. to remove phosgene from the reaction mixture, and the reaction mixture was concentrated upon evaporation under reduced pressure. Methylene chloride was added as an internal standard to the obtained residue, and the mixture was analyzed by $^1$H-NMR to estimate an amount of the produced chloroformate.

In addition, an amount of the produced phosgene was similarly estimated except that the cycle of the irradiation of a high energy light and the abeyance was repeated 2 times at 20° C. or 30° C. without applying ultrasound for comparison. The result is shown in Table 2.

TABLE 2

| Amount of $CHCl_3$ | Amount of 1-hexanol | Ultrasound application | Reaction temperature | Reaction time | Yield |
|---|---|---|---|---|---|
| 20 mL (250 mmol) | 10 mmol | OFF | 20° C. | 2 hr | 40% |
| 20 mL (250 mmol) | 10 mmol | OFF | 30° C. | 2 hr | 76% |
| 20 mL (250 mmol) | 10 mmol | ON | 20° C. | 2 hr | 97% |

The amount of the produced phosgene from chloroform was clearly increased by applying ultrasound in addition to irradiation of a high energy light as the result shown in Table 2. The amount of the produced phosgene was increased by increasing the reaction temperature without applying ultrasound, but the effect thereby was limited in comparison with the case of applying ultrasound.

Example 3: Promoting Effect of Phosgene Production by Ultrasound and High Energy Light

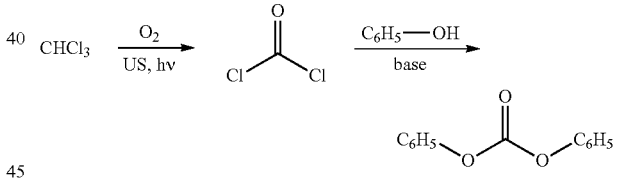

Purified chloroform (20 mL, 250 mmol), phenol (0.94 q, 10 mmol) and 5 M sodium hydroxide aqueous solution (20 mL, 100 mmol) were added in the reaction vessel of the reaction system used in Example 1. The reaction vessel was immersed in the water bath of an ultrasound washer ("1510J-MT" manufactured by BRANSONIC), and oxygen gas was blown by bubbling at 0.5 L/min with applying ultrasound of 70 W and 42 kHz and irradiating a high energy light from the low pressure mercury lamp at 20° C. for the reaction for 2 hours. The application of ultrasound and the high energy light was stopped after the reaction, extraction was carried out using chloroform, and the extract was dried over anhydrous sodium sulfate. The anhydrous sodium sulfate was removed by filtration, the filtrate was concentrated upon evaporation under reduced pressure, and the residue was dried in vacuo at 60° C. for 1 hour to obtain diphenyl carbonate as the target compound. The yield to the phenol as the raw material was calculated.

In addition, diphenyl carbonate was synthesized in the condition shown in Table 3 for comparison. The result is shown in Table 3.

TABLE 3

| Amount of CHCl₃ | Amount of phenol | Ultrasound application | Reaction time | Yield (vs phenol) |
|---|---|---|---|---|
| 20 mL (250 mmol) | 10 mmol | OFF | 3 hr | 55% |
| 20 mL (250 mmol) | 10 mmol | ON | 2 hr | 77% |
| 20 mL (250 mmol) | 20 mmol | ON | 2 hr | 66% |
| 20 mL (250 mmol) | 30 mmol | ON | 3 hr | 46% |

The amount of the produced phosgene from chloroform was clearly increased by applying ultrasound in addition to irradiation of a high energy light as the result shown in Table 3.

When a relative amount of phenol to chloroform was increased, the yield tended to become lower. The increased amount of the produced diphenyl carbonate in the reaction mixture was smaller than the increased amount of the phenol used as the raw material compound. The reason may be that the decomposition of chloroform was somewhat inhibited with increasing the relative amount of phenol, since an alcohol is used as a stabilizer of chloroform.

Example 4: Synthesis of bis(pentafluorophenyl)carbonate

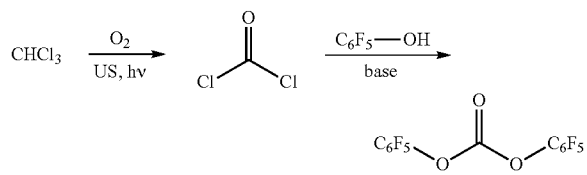

Purified chloroform (40 mL, 500 mmol), pentafluorophenol (10 mmol) and pyridine (50 mmol) were added in the reaction vessel of the reaction system used in Example 1. The reaction vessel was immersed in the water bath of an ultrasound washer ("1510J-MT" manufactured by BRAN-SONIC), and oxygen gas was blown by bubbling at 0.5 L/min with applying ultrasound of 70 W and 42 kHz and irradiating a high energy light from the low pressure mercury lamp at 30° C. for the reaction for 30 minutes or 1 hour.

Then, the temperature of the reaction mixture after the reaction was increased to 50° C. to remove phosgene from the reaction mixture, and the reaction mixture was concentrated upon evaporation under reduced pressure. Methylene chloride was added as an internal standard to the obtained residue, and the mixture was analyzed by ¹H-NMR to estimate an amount of the produced carbonate.

In addition, an experiment was similarly carried out except that the reaction mixture was stirred without applying ultrasound for comparison. The result is shown in Table 4.

TABLE 4

| Amount of CHCl₃ | Amount of PFP | Ultrasound application | Reaction time | Yield (vs PFP) |
|---|---|---|---|---|
| 40 mL (500 mmol) | 10 mmol | OFF | 0.5 hr | 29% |
| 40 mL (500 mmol) | 10 mmol | ON | 0.5 hr | 80% |
| 40 mL (500 mmol) | 10 mmol | ON | 1 hr | 89% |

The amount of the produced phosgene from chloroform was increased and the carbonate could be obtained in high yield by applying ultrasound in addition to irradiation of high energy light as the result shown in Table 4.

Example 5: Synthesis of bis(hexafluoroisopropyl)carbonate

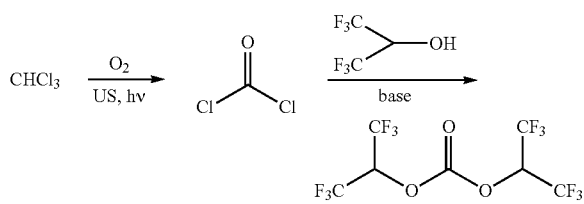

Purified chloroform (20 mL, 250 mmol), hexafluoroisopropanol (20 mmol) and pyridine (24 mmol) were added in the reaction vessel of the reaction system used in Example 1. The reaction vessel was immersed in the water bath of an ultrasound washer ("1510J-MT" manufactured by BRAN-SONIC), and oxygen gas was blown by bubbling at 0.5 L/min with applying ultrasound of 70 W and 42 kHz and irradiating a high energy light from the low pressure mercury lamp at 30° C. for the reaction for 1 hour or 1.5 hours. Then, the temperature of the reaction mixture after the reaction was increased to 50° C. to remove phosgene from the reaction mixture, and the temperature was decreased to room temperature. Next, methylene chloride was added as an internal standard to the obtained residue, and the mixture was analyzed by ¹H-NMR to estimate an amount of the produced carbonate. The result is shown in Table 5.

TABLE 5

| Amount of CHCl₃ | Amount of HFIP | Ultrasound application | Reaction time | Yield (vs (F₃C)₂CHOH) |
|---|---|---|---|---|
| 20 mL (250 mmol) | 20 mmol | ON | 1.0 hr | 83% |
| 20 mL (250 mmol) | 20 mmol | ON | 1.5 hr | 94% |

The amount of the produced phosgene from chloroform was increased and the carbonate could be obtained in high yield by applying ultrasound in addition to irradiation of high energy light as the result shown in Table 5.

Example 6: Promoting Effect of Phosgene Production by Ultrasound

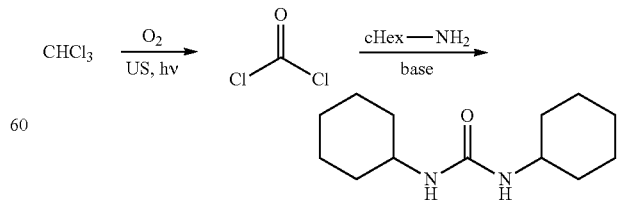

Purified chloroform (20 mL, 250 mmol) and cyclohexylamine (1 mL, 8.7 mmol) were added in a two-neck round-bottom flask. The reaction vessel was immersed in the water bath of an ultrasound washer ("1510J-MT" manufactured by BRANSONIC), and oxygen gas was blown by bubbling at 0.5 L/min with applying ultrasound of 70 W and 42 kHz under an ordinary room light at the temperature shown in Table 6 for the reaction for 16 hours.

Saturated sodium hydrogencarbonate aqueous solution and chloroform were added to the reaction mixture after the reaction, and the organic phase and the aqueous phase were separated. The obtained organic phase was dried and concentrated upon evaporation under reduced pressure. The obtained residue was dispersed in acetone for decoloration and filtrated to obtain dicyclohexylurea as an ash gray solid. The amount and the yield are shown in Table 6.

| Amount of $CHCl_3$ | Amount of cHex amine | Reaction temperature | Amount | Yield (vs amine) |
|---|---|---|---|---|
| 20 mL (250 mmol) | 1 mL (8.7 mmol) | 8° C. | 4 mg | 0.4% |
| 20 mL (250 mmol) | 1 mL (8.7 mmol) | 45° C. | 40 mg | 4.1% |
| 20 mL (250 mmol) | 1 mL (8.7 mmol) | 50° C. | 0 mg | 0% |

Chloroform could be decomposed and phosgene could be obtained by applying ultrasound even under an ordinary room light without irradiation of a high energy light as the result shown in Table 6. When the temperature was too low, the decomposition reaction was difficult to proceed, and when the temperature was too high, phosgene might not be reacted with an amine compound due to its volatilization.

Example 7: Promoting Effect of Phosgene Production by Ultrasound

An experiment was carried out similarly to Example 6 except that a halogenated hydrocarbon was changed from chloroform to tetrachloromethane or tetrachloroethane. In addition, an experiment was similarly carried out without applying ultrasound for comparison. The result is shown in Table 7.

TABLE 7

| Halogenated hydrocarbon | Ultrasound application | Amount | Yield (vs amine) |
|---|---|---|---|
| $CCl_4$ | OFF | 18 mg | 1.8% |
| $CCl_4$ | ON | 45 mg | 4.6% |
| $CHCl_2CHCl_2$ | OFF | 0.4 mg | 0.04% |
| $CHCl_2CHCl_2$ | ON | 42 mg | 4.3% |

It was demonstrated by the result shown in Table 7 that even when a halogenated hydrocarbon other than chloroform is used under an ordinary room light, the halogenated hydrocarbon is decomposed to produce phosgene by applying ultrasound.

Example 8: Promoting Effect of Phosgene Production by Ultrasound

Bromoform (20 mL, 230 mmol) and cyclohexylamine (1 mL, 8.7 mmol) were added into a two-neck round-bottom flask. The reaction vessel was immersed in the water bath of an ultrasound washer ("1510J-MT" manufactured by BRANSONIC), and oxygen gas was blown by bubbling at 0.5 L/min with applying ultrasound of 70 W and 42 kHz under an ordinary room light at 50° C. for the reaction for 16 hours.

Saturated sodium hydrogencarbonate aqueous solution and chloroform were added to the reaction mixture after the reaction, and the organic phase and the aqueous phase were separated. The obtained organic phase was dried and concentrated upon evaporation under reduced pressure. The obtained residue was dispersed in acetone for decoloration and filtrated to obtain dicyclohexylurea as an ash gray solid. The yield to cyclohexylamine was calculated.

In addition, similar experiments were carried out in the conditions shown in Table 8 for comparison. When strong ultrasound was applied, the ultrasound washer was changed to "US-303" of 300 W and 38 kHz manufactured by SND. The amount and yield are shown in Table 8.

TABLE 8

| Amount of $CHBr_3$ | Amount of cHex amine | Ultrasound application | Supplied gas | Reaction time | Amount | Yield |
|---|---|---|---|---|---|---|
| 20 mL (230 mmol) | 1 mL (8.7 mmol) | ON | $O_2$ | 16 hr | 83 mg | 8.5% |
| 20 mL (230 mmol) | 1 mL (8.7 mmol) | ON | Ar | 16 hr | 0 mg | 0% |
| 20 mL (230 mmol) | 1 mL (8.7 mmol) | ON | $O_2$ | 48 hr | 132 mg | 13.5% |
| 20 mL (230 mmol) | 1 mL (8.7 mmol) | OFF | $O_2$ | 16 hr | 17 mg | 1.7% |
| 20 mL (230 mmol) | 1 mL (8.7 mmol) | Strong ultrasound ON | $O_2$ | 16 hr | 45 mg | 4.6% |

It was found by the result shown in Table 8 that when oxygen gas was not used, bromoform could not be decomposed even by applying ultrasound and bromophosgene was not produced. On the one hand, when ultrasound was applied with supplying oxygen gas, the reaction proceeded even under a general room light as bromoform could be decomposed and bromophosgene was produced.

In addition, when bromoform was used, the yield tended to be higher than that of the case that chloroform was decomposed by applying ultrasound under a general room light. The reason may be the difference between the binding energy of C—Cl bond in chloroform and the binding energy of C—Br bond in bromoform.

When strong ultrasound was applied, the yield tended to be lower. The reason may be that oxygen in the reaction mixture was removed into the air by ultrasound.

Example 9: Promoting Effect of Phosgene Production by Ultrasound

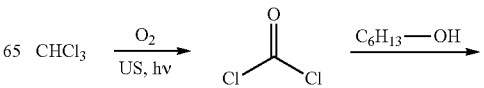

-continued

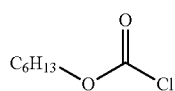

Purified chloroform (20 mL, 250 mmol) and 1-hexanol (1.25 mL, 10 mol) were added in the reaction vessel of the reaction system used in Example 1. The reaction vessel was immersed in the water bath of an ultrasound washer ("1510J-MT" manufactured by BRANSONIC), and the photoreaction vessel was equipped with 2 L oxygen gas bag for the reaction at 0° C. for 3 hours with applying ultrasound of 70 W and 42 kHz and irradiating a high energy light from the low pressure mercury lamp. Then, the temperature was increased to 50° C. to remove phosgene from the reaction mixture, and reaction mixture was concentrated upon evaporation under reduced pressure. Methylene chloride was added as an internal standard to the obtained residue, and the mixture was analyzed by $^1$H-NMR to estimate an amount of the produced chloroformate.

An amount of the produced chloroformate was similarly estimated except that ultrasound was not applied for comparison. The result is shown in Table 9.

TABLE 9

| Amount of $CHCl_3$ | Ultrasound application | Yield (vs hexanol) |
|---|---|---|
| 20 mL (250 mmol) | ON | 64% |
| 20 mL (250 mmol) | OFF | 37% |

It was demonstrated by the result shown in Table 9 that a halogenated hydrocarbon is efficiently decomposed to produce phosgene by applying ultrasound in the presence of a sufficient amount of oxygen in the gas phase even when oxygen gas is not blown into the reaction mixture.

Example 10: Promoting Effect of Phosgene Production by Ultrasound

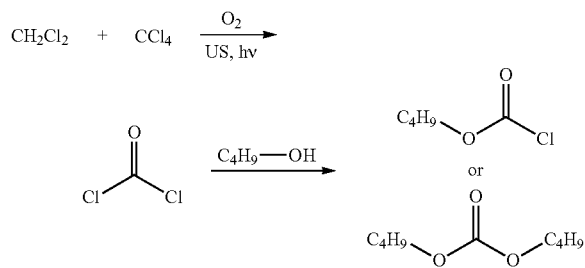

A quartz glass jacket having a diameter of 30 mm was centrally inserted into a cylindrical reaction vessel having a diameter of 70 mm, and a low pressure mercury lamp ("UVL20PH-6" manufactured by SEN Light, 20 W, φ24× 120 mm, wave length: 185 to 600 nm, peak wave length: 254 nm) was inserted in the quartz glass jacket. Dichloromethane (40 mL, 625 mmol) and tetrachloromethane (40 mL, 412 mmol) were added into the reaction vessel. The reaction vessel was immersed in the water bath of an ultrasound washer ("1510J-MT" manufactured by BRANSONIC), and oxygen gas was blown into the mixed solution of dichloromethane and tetrachloromethane by bubbling at 0.2 L/min from a PTFE tube with applying ultrasound of 70 W and 42 kHz and irradiating a high energy light from the low pressure mercury lamp at 25° C. for the reaction for 4 hours. Then, 1-butanol (1.3 mL, 10 mmol) was added in order to estimate an amount of the produced phosgene. The gas discharged from the reaction vessel was introduced into a butanol trap (25 mL, 273 mmol) to capture phosgene in the gas during the reaction.

The reaction mixture after the reaction was analyzed by $^1$H-NMR to estimate the amounts of the produced chloroformate and carbonate. The butanol trap solution was also analyzed by $^1$H-NMR to estimate the amounts of the produced chloroformate and carbonate. The amount of the produced phosgene was estimated and the yield of phosgene to the used dichloromethane and tetrachloromethane was calculated under the presumption that all of the produced phosgene was reacted with 1-butanol trap to be converted to the chloroformate or the carbonate.

In addition, an amount of the produced phosgene was similarly estimated in the condition that ultrasound was not applied for comparison. The result is shown in Table 10.

TABLE 10

| Amount of $CH_2CH_2$ | Amount of $CCl_4$ | Ultrasound application | Yield (vs $CH_2Cl_2$ + $CCl_4$) |
|---|---|---|---|
| 40 mL (625 mmol) | 40 mL (412 mmol) | ON | 2.3% |
| 40 mL (625 mmol) | 40 mL (412 mmol) | OFF | 1.5% |

It was demonstrated by the result shown in Table 10 that the decomposition of a halogenated hydrocarbon and the production of phosgene can be promoted by applying ultrasound even when two kinds of halogenated hydrocarbons are used.

EXPLANATION OF REFERENCES

1: Reaction vessel, 2: Light-irradiating means, 3: Water bath of ultrasound-generating device, 4: Jacket, 5: Cooling tube

The invention claimed is:

1. A method for producing a halogenated carbonyl, the method comprising the step of applying ultrasound to a composition containing a $C_{1-4}$ halogenated hydrocarbon having one or more halogeno groups selected from the group consisting of chloro, bromo and iodo under a stream of a gas containing oxygen or with supplying a gas containing oxygen into the composition by bubbling to decompose the $C_{1-4}$ halogenated hydrocarbon with or without irradiating a high energy light having a peak wavelength included in a range of 180 nm or more and 280 nm or less.

2. The method according to claim 1, wherein the high energy light having a peak wavelength included in a range of 180 nm or more and 280 nm or less is irradiated to the composition.

3. The method according to claim 1, wherein a frequency of the ultrasound is 20 kHz or more and 100 kHz or less.

4. The method according to claim 1, wherein power of the ultrasound applied to the composition is 0.05 W/cm$^2$ or more and 10 W/cm$^2$ or less per a surface area of the composition to which the ultrasound is applied.

5. The method according to claim 1, wherein a $C_{1-2}$ polyhalogenated hydrocarbon is used as the $C_{1-4}$ halogenated hydrocarbon.

6. The method according to claim 1, wherein a mixture of dichloromethane and tetrachloromethane is used as the $C_{1-4}$ halogenated hydrocarbon.

7. The method according to claim 2, wherein a $C_{1-2}$ polyhalogenated hydrocarbon is used as the $C_{1-4}$ halogenated hydrocarbon.

8. The method according to claim 2, wherein a mixture of dichloromethane and tetrachloromethane is used as the $C_{1-4}$ halogenated hydrocarbon.

\* \* \* \* \*